US012650420B2

(12) United States Patent
Satterfield

(10) Patent No.: US 12,650,420 B2
(45) Date of Patent: Jun. 9, 2026

(54) LUBRICATING OIL ANALYSIS

(71) Applicant: ExxonMobil Technology and Engineering Company, Annandale, NJ (US)

(72) Inventor: Andrew Satterfield, Furlong, PA (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 444 days.

(21) Appl. No.: 18/480,346

(22) Filed: Oct. 3, 2023

(65) Prior Publication Data

US 2024/0133859 A1 Apr. 25, 2024

Related U.S. Application Data

(60) Provisional application No. 63/379,245, filed on Oct. 12, 2022.

(51) Int. Cl.
*G01N 33/28* (2006.01)
*G01N 23/223* (2006.01)

(52) U.S. Cl.
CPC ....... *G01N 33/2888* (2013.01); *G01N 23/223* (2013.01); *G01N 2223/076* (2013.01); *G01N 2223/1016* (2013.01); *G01N 2223/637* (2013.01); *G01N 2223/652* (2013.01)

(58) Field of Classification Search
CPC ............. G01N 33/2888; G01N 23/223; G01N 2223/076; G01N 2223/1016; G01N 2223/637; G01N 2223/652
See application file for complete search history.

(56) References Cited

U.S. PATENT DOCUMENTS

| | | | |
|---|---|---|---|
| 6,779,505 B2 | 8/2004 | Reischam et al. | |
| 6,874,459 B2 | 4/2005 | Carey et al. | |
| 7,316,992 B2 | 1/2008 | Natoli et al. | |
| 10,975,739 B2 | 4/2021 | Claussen et al. | |
| 2003/0159672 A1* | 8/2003 | Carey ..................... | F16N 39/08 |
| | | | 123/196 R |

(Continued)

FOREIGN PATENT DOCUMENTS

| | | | | |
|---|---|---|---|---|
| KR | 101425832 B1 * | 7/2014 | .......... | C10M 163/00 |
| WO | 2015036543 A1 | 3/2015 | | |
| WO | 2017067561 A1 | 4/2017 | | |

*Primary Examiner* — Francis C Gray

(74) *Attorney, Agent, or Firm* — Vorys, Sater, Seymour and Pease LLP

(57) ABSTRACT

A method of analyzing a lubricating oil may include: measuring a first concentration of components in a lubricating oil prior to introduction into a cylinder in a two-stroke engine using x-ray fluorescence, the components comprising: sulfur and total calcium; collecting a scrape-down lubricating oil that corresponds to the lubricating oil after having been passed through the cylinder during fuel combustion of a fuel comprising 0.5 wt % or less sulfur; measuring a second concentration of the components in the scrape-down lubricating oil using the x-ray fluorescence; and calculating an amount of acid neutralized during combustion based on the first and second concentration of the components. Based on said analysis a change to a property of the scrape-down lubricating oil and/or changing a feed rate of the lubricating oil into the cylinder based on the amount of acid neutralized may be implemented.

19 Claims, 9 Drawing Sheets

(56)                References Cited

U.S. PATENT DOCUMENTS

| | | | |
|---|---|---|---|
| 2003/0194811 A1* | 10/2003 | Reischman | ............ G01N 21/33 |
| | | | 436/171 |
| 2007/0196925 A1* | 8/2007 | Reischman | ........ G01N 33/2876 |
| | | | 436/60 |
| 2008/0207474 A1 | 8/2008 | Damm et al. | |
| 2019/0187119 A1* | 6/2019 | Christensen | ......... G01N 33/287 |
| 2020/0340934 A1 | 10/2020 | Juston et al. | |

* cited by examiner

LUBRICATING OIL ANALYSIS

FIELD OF INVENTION

The present disclosure relates to methods and systems for analyzing lubricating oil, especially marine lubricating oil used in combination with low sulfur fuels.

BACKGROUND

Many conventional marine fuels correspond to fuels having a substantial sulfur content. During combustion to operate a diesel engine, the sulfur can be oxidized to form sulfuric acid. This can lead to undesirable corrosion of surfaces and/or seals within the engine if the sulfuric acid can condense on a surface. In order to mitigate this problem, bases such as calcium carbonate can be added to the lubricants used for a marine engine. The fuel and lubricants can interact in the combustion cylinder, so if sufficient base is added to the lubricant, the sulfuric acid formed during combustion of the fuel can be neutralized if it condenses. Total base number is often used as an indicator of the capacity for a lubricant (or other hydrocarbon fluid) to neutralize additional acid. In other words, total base number is a measure of reserve alkalinity. A used lubricating oil can refer to a lubricating oil after it has passed through an engine cylinder while performing a combustion reaction to operate the engine. A scrape-down oil is an example of a used marine lubricating oil.

Traditional determination of the total base number uses techniques like titration, chemical reaction, chemometric modeling, and more recently based on elemental measurements of calcium and sulfur combined with elemental iron measurement. These measurements are typically performed in labs and not at the site of the engine, which often means results take at least a week to be reported. If the oil analysis indicates a need for change in operating conditions, the delay in reporting can result in potential damage and wear to the engine.

An alternative method for characterizing whether sufficient base has been added to a lubricant is based on the total base number of the scrape-down oil that remains after combustion. U.S. Pat. No. 7,741,122 describes a method for estimating the total base number of marine scrape-down oil by determining the sulfur content of the scrape-down oil using x-ray fluorescence. Optionally, calcium in the scrape-down oil can also be determined, with the measured value being used to normalize the sulfur values between samples. Although the method allows for an estimate of residual total base number, the minimum amount of sulfur in the fuel needed for a reliable estimate of residual total base number is relatively high, typically about 2 wt % or more. However, recent policies limit the amount of sulfur in a marine fuel to 0.5 wt % unless vessels are equipped with scrubbers to remove sulfuric acid from the exhaust. Less sulfur in the fuel means less acid is produced during combustion. Accordingly, less total base is needed in the lubricant. If too low a base number lubricant oil is used, the sulfuric acid not neutralized leads to corrosion. If too high a base number is used, the excess inorganic base, such as calcium carbonate, may form deposits that accumulate on the interior of the engine, which may cause physical wear and damage to engine parts and lead to decreases in efficiency.

SUMMARY OF INVENTION

A nonlimiting example method of the present disclosure comprises: measuring a first concentration of components in a lubricating oil prior to introduction into a cylinder in a two-stroke engine using x-ray fluorescence, the components comprising: sulfur and total calcium; collecting a scrape-down lubricating oil that corresponds to the lubricating oil after having been passed through the cylinder during fuel combustion of a fuel comprising 0.5 wt % or less sulfur; measuring a second concentration of the components in the scrape-down lubricating oil using the x-ray fluorescence; calculating an amount of acid neutralized during combustion based on the first and second concentration of the components; and implementing a change to a property of the scrape-down lubricating oil and/or changing a feed rate of the lubricating oil into the cylinder based on the amount of acid neutralized.

Another nonlimiting example method of the present disclosure comprises: measuring a first concentration of components in a lubricating oil prior to introduction into a cylinder in an engine using x-ray fluorescence, the components comprising: sulfur and total calcium; collecting a scrape-down lubricating oil that corresponds to the lubricating oil after having been passed through the cylinder during fuel combustion of a fuel comprising 0.5 wt % or less sulfur; measuring a second concentration of the components in the scrape-down lubricating oil using the x-ray fluorescence; calculating an amount of acid neutralized during combustion based on the first and second concentration of the components; calculating a remaining useful base number for the scrape-down lubricating oil; and implementing a change to a property of the scrape-down lubricating oil and/or changing a feed rate of the lubricating oil into the cylinder based on the remaining useful base number.

Yet another nonlimiting example method of the present disclosure comprises: measuring a first concentration of components in a lubricating oil prior to introduction into a cylinder in an engine using x-ray fluorescence, the components comprising: sulfur and total calcium; collecting a scrape-down lubricating oil that corresponds to the lubricating oil after having been passed through the cylinder during fuel combustion of a fuel comprising 0.5 wt % or less sulfur; measuring a second concentration of the components in the scrape-down lubricating oil using the x-ray fluorescence; calculating an amount of acid neutralized during combustion based on the first and second concentration of the components; calculating a total base number for the scrape-down lubricating oil; and implementing a change to a property of the scrape-down lubricating oil and/or changing a feed rate of the lubricating oil into the cylinder based on a correlation between the amount of acid neutralized during combustion and the total base number for the scrape-down lubricating oil.

Another nonlimiting example method of the present disclosure comprises: measuring a first metal concentration in a marine lubricating oil prior to introduction into a cylinder in an engine using x-ray fluorescence, wherein the first metal concentration includes a concentration of soluble metal and a concentration of insoluble metal; collecting a scrape-down marine lubricating oil that corresponds to the marine lubricating oil after having been passed through the cylinder during fuel combustion of a fuel comprising 0.5 wt % or less sulfur; measuring a second metal concentration in the scrape-down marine lubricating oil using the x-ray fluorescence; calculating a change in metal concentration during combustion based on the first and second metal concentration; and when the change in metal concentration is an increase in the metal concentration that is above a threshold, implementing a change to a property of the scrape-down marine lubricating oil and/or changing a feed rate of the lubricating oil into the cylinder to cause a reduction in a base number of the lubricating oil in the engine.

These and other features and attributes of the disclosed methods and systems of the present disclosure and their advantageous applications and/or uses will be apparent from the detailed description which follows.

BRIEF DESCRIPTION OF THE DRAWINGS

To assist those of ordinary skill in the relevant art in making and using the subject matter hereof, reference is made to the appended drawings. The following figures are included to illustrate certain aspects of the disclosure, and should not be viewed as exclusive configurations. The subject matter disclosed is capable of considerable modifications, alterations, combinations, and equivalents in form and function, as will occur to those skilled in the art and having the benefit of this disclosure.

DETAILED DESCRIPTION

Figure 1:
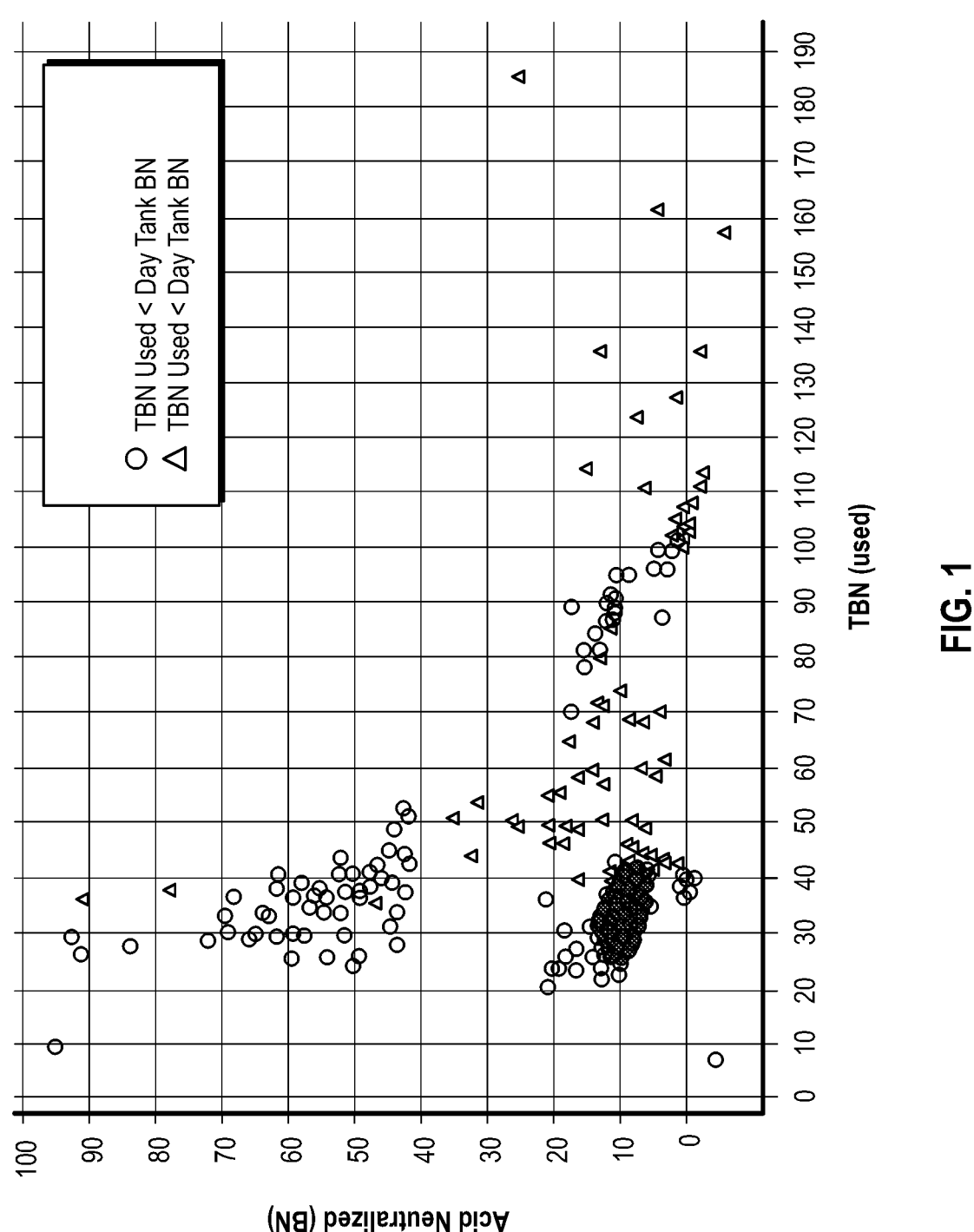
FIG. 1 is a plot of total base number of a scrape-down marine lubricant oil as a function of the amount of acid resultant from combustion of sulfur-containing fuel neutralized by the lubricant oil.

The present disclosure relates to methods and systems for analyzing lubricating oil, especially marine lubricating oil used in combination with low sulfur fuels in two-stroke engines.

All numerical values within the detailed description and the claims herein are modified by "about" or "approximately" the indicated value, and take into account experimental error and variations that would be expected by a person having ordinary skill in the art. The phrase "major amount" or "major component" as it relates to components included within the lubricating oils of the specification and the claims means greater than or equal to 50 wt %, or greater than or equal to 60 wt %, or greater than or equal to 70 wt %, or greater than or equal to 80 wt %, or greater than or equal to 90 wt % based on the total weight of the lubricating oil. The phrase "minor amount" or "minor component" as it relates to components included within the lubricating oils of the specification and the claims means less than 50 wt %, or less than or equal to 40 wt %, or less than or equal to 30 wt %, or greater than or equal to 20 wt %, or less than or equal to 10 wt %, or less than or equal to 5 wt %, or less than or equal to 2 wt %, or less than or equal to 1 wt %, based on the total weight of the lubricating oil. The phrase "essentially free" as it relates to components included within the lubricating oils of the specification and the claims means that the particular component is at 0 weight % within the lubricating oil, or alternatively is at impurity type levels within the lubricating oil (less than 100 ppm, or less than 20 ppm, or less than 10 ppm, or less than 1 ppm). The phrase "other lubricating oil additives" as used in the specification and the claims means other lubricating oil additives that are not specifically recited in the particular section of the specification or the claims. For example, other lubricating oil additives may include, but are not limited to, antioxidants, detergents, dispersants, antiwear additives, corrosion inhibitors, viscosity modifiers, metal passivators, pour point depressants, seal compatibility agents, antifoam agents, extreme pressure agents, friction modifiers and combinations thereof.

Diesel engines may generally be classified as slow-speed, medium-speed, or high-speed engines, with the slow-speed variety being used for the largest, deep draft marine vessels and in industrial applications. Slow-speed diesel engines are typically direct coupled, direct reversing, two-stroke cycle engines operating in the range of about 57 rpm to 250 rpm and usually run on residual fuels. These engines are of crosshead construction with a diaphragm and stuffing boxes separating the power cylinders from the crankcase to prevent combustion products from entering the crankcase and mixing with the crankcase oil. Medium-speed engines typically operate in the range of 250 rpm to about 1100 rpm and may operate on the 2-stroke or 4-stroke cycle. These engines are trunk piston design, and many operate on residual fuel as well. They may also operate on distillate fuel containing little or no residuals. On deep-sea vessels these engines may be used for propulsion, ancillary applications or both. Slow-speed and medium-speed marine diesel engines are also extensively used in power plant operations and the methods disclosed herein are also applicable in these applications.

Each type of diesel engine employs lubricating oils to minimize component wear, remove heat, neutralize and disperse combustion products, prevent rust and corrosion, and prevent sludge formation or deposits. For some lubricant applications, such as in lubricating cylinders in low-speed, crosshead diesel engines that employ all-loss lubrication systems and combust heavy fuel oil with widely varying sulfur contents, the primary cause of engine wear is in acid induced corrosive wear. Lubricants for these fuels are formulated to have a high total base number (TBN) to neutralize the acids formed by combusting these fuels so as to minimize corrosive wear of these engines. TBN is an indicator of the capacity for a lubricant (or other hydrocarbon fluid) to neutralize additional acid. In other words, total base number is a measure of reserve alkalinity. In this discussion, measured values for total base number are determined according to ASTM D2896. The units of total base number correspond to mg KOH per gram of lubricant.

However, in low-sulfur fuels (e.g., fuels comprising sulfur at less than 0.5 wt % or less), less sulfuric acid is produced during combustion and the unconsumed bases, especially calcium carbonate, present in the lubricants may precipitate during use and form deposits that accumulate on the interior of the engine (e.g., a two-stroke engine), potentially impacting efficiency and which may cause physical wear and damage to engine parts. The traditional methods to determine TBN of scrape-down oil often employ non-aqueous titrations and measuring elemental Calcium concentration is typically done using inductively coupled plasma (ICP). Both techniques do not account for the insoluble (or precipitated) calcium carbonate. Therefore, the TBN used for adjusting the lubricant composition (e.g., by inclusion of more base, changing feed rate of fresh lubricant, or the like) is wrong and, in some instances, significantly lower than expected. Consequently, more base may be added, which further contributes to the insoluble calcium carbonate wear issues.

Because low sulfur fuels can lead to incorrect TBN values for lubricants, the present disclosure uses the amount of acid neutralized to characterize the scrape-down lubricating oil. The amount of acid neutralized (A.N.) may be calculated according to $$A.N. = \alpha * S_{used} - (\alpha * S_{fresh}) * \left(\frac{M_{used}}{M_{fresh}}\right) \qquad \text{EQ. 1}$$

where A.N. is acid neutralized (mg KOH/g lubricant), $\alpha$ is a constant value of 35 (mg KOH)/(g lubricant*wt % S) for converting from units of sulfur concentration to units of mg KOH/g lubricant, $S_{used}$ is the concentration of sulfur in the scrape-down lubricating oil (wt %), $S_{freash}$ is the concentration of sulfur in the lubricating oil prior to introduction into a cylinder in an engine h is (wt %), $M_{used}$ is the concentration of metal (e.g., Ti, Ca, and the like) in the scrape-down lubricating oil (wt %), and $M_{fresh}$ is the concentration of metal in the lubricating oil prior to introduction into a cylinder in an engine (wt %).

A metal-specific A.N may be EQ. 2, which is specific to calcium.

$$A.N. = \alpha * S_{used} - (\alpha * S_{fresh}) * \left(\frac{Ca_{used}}{Ca_{fresh}}\right) \qquad \text{EQ. 2}$$

where A.N. is acid neutralized (mg KOH/g lubricant), $\alpha$ is a constant value of 35 (mg KOH)/(g lubricant*wt % S) for converting from units of sulfur concentration to units of mg KOH/g lubricant, $S_{used}$ is the concentration of sulfur in the scrape-down lubricating oil (wt %), S fresh is the concentration of sulfur in the lubricating oil prior to introduction into a cylinder in an engine (wt %), Ca used is the concentration of calcium in the scrape-down lubricating oil (wt %), and $Ca_{fresh}$ is the concentration of calcium in the lubricating oil prior to introduction into a cylinder in an engine (wt %).

If total base number were expressed with respect to a different base (such as NaOH), the value of $\alpha$ would correspondingly change.

The foregoing calcium concentrations should be the total calcium (i.e., soluble and insoluble calcium) in the sample. To mitigate errors in this value due to settling of insoluble calcium, the measurement is preferably taken soon after acquiring the scrape-down lubricating oil sample. Said time between collection of the scrape-down lubricating oil sample and measurements may be about 4 hours or less (or about 1 minute or less, or about 5 minutes or less, or about 10 minutes or less, or about 15 minutes or less, or about 30 minutes or less, or about 1 minute to about 1 hour, or about 30 minutes to about 4 hours, or about 1 minute to about 10 minutes, or about 5 minutes to about 30 minutes, or about 20 minutes to about 1 hour, or about 1 hour to about 4 hours).

Measurement of the sulfur and calcium concentrations may be performed using x-ray fluorescence (XRF). XRF may be used for measuring the concentration of calcium and sulfur as well other elements like iron, chromium, vanadium, magnesium, phosphorus, chlorine, potassium, manganese, aluminum, silicon, titanium, copper, nickel, zinc, lead, tin, or other elements. XRF may be performed according the method in ASTM D6443-14(2019)e1. It is noted that ASTM D6443-14(2019)e1 is traditionally used for determination of elemental quantities in fresh lubricating oils, but in some aspects it can also be used for determination of an element content in a scrape-down lubricating oil, so that the same method is used for determination of element content in both a fresh lubricant oil and the corresponding scrape-down lubricating oil. For elements not specifically identified in ASTM D6443-14(2019)e1, the XRF elemental analysis may be performed in a similar method.

The amount of acid neutralized during combustion determined for the scrape-down lubricating oil may be used to determine a change to a property of the scrape-down lubricating oil and/or changing a feed rate of the lubricating oil into the cylinder based on the amount of acid neutralized.

For example, if the amount of acid neutralized during combustion is above a first threshold, the high value can indicate a likelihood of the presence of sulfuric acid within the combustion cylinder environment. This can cause undesirable corrosion of the cylinder walls. Alternatively, if the amount of acid neutralized during combustion is below a second threshold value, the low value can indicate that too much oil is being delivered to the cylinders and/or that too much base is present in the lubricating oil. Thus, after calculating the amount of acid neutralized during combustion, the resulting value can be used to perform one or more corrective actions. In some aspects, the corrective action can correspond to adjusting the oil flow rate to the cylinder(s). If the amount of acid neutralized during combustion is too high, such as more than a first threshold value (or higher threshold), the flow rate of lubricant to the cylinder(s) can be increased. Although the fresh oil is not changed, the higher flow rate means that more base is delivered to the cylinder. Similarly, if the amount of acid neutralized during combustion is too low, such as less than a second threshold (or lower threshold), the flow rate of lubricant to the cylinder(s) can be decreased. This can save on operating costs for the vessel and reduce the volume of waste used oil produced. In some aspects, the first threshold and/or the second threshold for the scrape-down lubricating oil can be selected based on the total base number for the corresponding fresh oil. One example of selecting a threshold value based on the total base number for the corresponding fresh oil can be to select a threshold value based on a percentage of the total base number for the corresponding fresh oil (i.e., multiplying the total base number for the fresh oil by a scaling factor). In various aspects, the second threshold value can be 20 mg KOH/g or less, or 15 mg KOH/g or less, or 10 mg KOH/g or less, such as down to roughly 0 mg KOH/g. If the calculated acid number falls below the second threshold value, less base or detergent (such as $CaCO_3$) can be added to the fresh oil to decrease the total base number of the fresh oil by 5 mg KOH/g or more, or 10 mg KOH/g, or 15 mg KOH/g or more, such as up to 25 mg KOH/g or still higher.

Therefore, a method of the present disclosure may include: measuring a first concentration of components in a lubricating oil (e.g., marine lubricating oil) prior to introduction into a cylinder in an engine (e.g., a two-stroke engine) using XRF, the components comprising: sulfur and total calcium; collecting a scrape-down lubricating oil that corresponds to the lubricating oil after having been passed through the cylinder during fuel combustion of a fuel comprising 0.5 wt % or less sulfur (or 0.1 wt % or less sulfur, or 0.01 wt % to 0.5 wt % sulfur, or 0.01 wt % to 0.1 wt % sulfur); measuring a second concentration of the components in the scrape-down lubricating oil within about 4 hours of the collecting of the scrape-down lubricating oil using the XRF; calculating an amount of acid neutralized during combustion based on the first and second concentration of the components; and implementing a change to a property of the scrape-down lubricating oil and/or changing a feed rate of the lubricating oil into the cylinder based on the amount of acid neutralized.

In another example of using the amount of acid neutralized during combustion allows one to calculate the remaining useful base number in the scrape-down lubricating oil. From that, an operator may change a property of the scrape-down lubricating oil and/or change a feed rate of the lubricating oil. The remaining useful base number (R.U.B.N.) may be calculated according to EQ. 3 where TBNf resh is calculated according to EQ. 4 using XRF or traditional measurement techniques (e.g., titration via ASTM D2896-21 or ICP techniques).

$$R.U.B.N. = TBN_{fresh} - A.N. \qquad \text{EQ. 3}$$

$$TBN_{fresh} = A * Ca_{fresh} + B \qquad \text{EQ. 4}$$

where A and B are factors that may be determined experimentally, where A is a weighting factor for calcium (typically about 26.8 per weight percent calcium) and B is a correction for other base components (e.g., other metals or ashless sources of base number) in the lubricating oil.

A high R.U.B.N. may indicate that less base (e.g., by decreasing the feed rate and/or by using a lower base number lubricant) is needed to neutralize acid.

A method of the present disclosure may include: measuring a first concentration of components in a lubricating oil (e.g., a marine lubricating oil) prior to introduction into a cylinder in an engine (e.g., a two-stroke engine) using x-ray fluorescence, the components comprising: sulfur and total calcium; collecting a scrape-down lubricating oil (e.g., a scrape-down marine lubricating oil) that corresponds to the lubricating oil after having been passed through the cylinder during fuel combustion of a fuel comprising 0.5 wt % or less sulfur (or 0.1 wt % or less sulfur, or 0.01 wt % to 0.5 wt % sulfur, or 0.01 wt % to 0.1 wt % sulfur); measuring a second concentration of the components in the scrape-down lubricating oil within about 4 hours of the collecting of the scrape-down lubricating oil using the x-ray fluorescence; calculating an amount of acid neutralized during combustion based on the first and second concentration of the components; calculating a remaining useful base number for the scrape-down lubricating oil; and implementing a change to a property of the scrape-down lubricating oil and/or changing a feed rate of the lubricating oil into the cylinder based on the remaining useful base number.

In yet another example of using the amount of acid neutralized during combustion, a relationship between the total base number of the scrape-down lubricating oil (e.g., the scrape-down marine lubricating oil) and the amount of acid neutralized during combustion may be used to ascertain potential issues (e.g., the presences of high concentrations of calcium carbonate deposits). For example, high TBN values for the scrape-down lubricating oil (e.g., greater than the TBN of the fresh oil) with low values for the amount of acid neutralized during combustion may indicate insoluble calcium is forming and corrective action to the composition of the lubricating oil and/or a feed rate of the lubricating oil should be taken to reduce the amount of insoluble calcium, which mitigates wear of the engine. Wear may be indicated by measuring metals (e.g., iron, chromium or other metals) being in the scrape-down oil. Decreasing the excess calcium in the used oil may show a decrease in wear metals. The TBN for the scrape-down lubricating oil (TBN use d) may be determined according to EQ. 5 or EQ. 6 where sulfur and calcium concentrations are determined using XRF as discussed above and $TBN_{fresh}$ may be measured using XRF or traditional measurement techniques (e.g., titration via ASTM D2896-21 or ICP techniques).

$$TBN_{used} = (26.8 * Ca_{fresh} + \alpha * S_{fresh}) \frac{Ca_{used}}{Ca_{fresh}} - 35 * S_{used} \qquad \text{EQ. 5}$$

$$TBN_{used} = (TBN_{fresh} + \alpha * S_{fresh}) \frac{Ca_{used}}{Ca_{fresh}} - 35 * S_{used} \qquad \text{EQ. 6}$$

For example, a high $TBN_{used}$ (e.g., greater than about 100 mg KOH/g lubricant) corresponding to a low A.N. (e.g., less than about 30 mg KOH/g lubricant) when using a lubricating oil with a fresh BN of 100, may indicate that significant amounts of calcium carbonate are forming solid particulates and causing wear to the engine. Further, a low TBN use d (e.g., less than about 50 mg KOH/g lubricant) and a low A.N. (e.g., less than about 30 mg KOH/g lubricant) may indicate that appropriate conditions and compositions are in place and should be maintained.

A method of the present disclosure may comprise: measuring a first concentration of components in a lubricating oil (e.g., a marine lubricating oil) prior to introduction into a cylinder in an engine (e.g., a two-stroke engine) using x-ray fluorescence, the components comprising: sulfur and total calcium; collecting a scrape-down lubricating oil (e.g., a scrape-down marine lubricating oil) that corresponds to the lubricating oil after having been passed through the cylinder during fuel combustion of a fuel comprising 0.5 wt % or less sulfur (or 0.1 wt % or less sulfur, or 0.01 wt % to 0.5 wt % sulfur, or 0.01 wt % to 0.1 wt % sulfur); measuring a second concentration of the components in the scrape-down lubricating oil within about 4 hours of the collecting of the scrape-down lubricating oil using the x-ray fluorescence; calculating an amount of acid neutralized during combustion based on the first and second concentration of the components; calculating a total base number for the scrape-down lubricating oil; and implementing a change to a property of the scrape-down lubricating oil and/or changing a feed rate of the lubricating oil into the cylinder based on a correlation between the amount of acid neutralized during combustion and the total base number for the scrape-down lubricating oil.

In alternative embodiments, metal alone, or optionally in combination with A.N. (using calcium and sulfur concentrations), may be used when analyzing the lubricating oil. In this example, a change in the concentration of a metal may be used where a threshold change in metal concentration is set such that too high of a metal concentration change may indicate that base and/or calcium precipitates are building up in the lubricating oil (e.g., a marine lubricating oil). Accordingly, a change to a property of the scrape-down lubricating oil and/or changing a feed rate of the lubricating oil into the cylinder to cause a reduction in a base number of the lubricating oil in the engine may mitigate reduce the formation of precipitates that cause wear in the engine. A nonlimiting example equation for analyzing a change in a metal concentration is provided in EQ. 7 (specifically calcium in EQ. 8).

$$\Delta M = \left( \left( \frac{M_{used}}{M_{fresh}} \right) - 1 \right) * 100 \qquad \text{EQ. 7}$$

-continued $$\Delta Ca = \left( \left( \frac{Ca_{used}}{Ca_{fresh}} \right) - 1 \right) * 100 \qquad \text{EQ. 8}$$

where $\Delta M$ and $\Delta Ca$ are a percentage, and M is a metal.

Examples of metals may include, but are not limited to, calcium, iron, chromium, vanadium, magnesium, phosphorus, chlorine, potassium, manganese, aluminum, silicon, titanium, copper, nickel, zinc, lead, tin, and the like. The threshold may depend on the metal. For example, when using calcium, a threshold for a percent change in metal concentration (per EQ. 7) may be 20% (or 18%, or 15%). Exceeding said threshold (e.g., reporting a change in calcium of 22%) may trigger a remedial action to reduce the base number of the lubricating oil in the engine, for example, by increasing a feed rate of fresh lubricating oil and/or by changing to a fresh lubricating oil with a lower base number but maintaining (or also increasing) the feed rate of fresh lubricating oil.

The methods of using a metal to analyze the lubricating oil, while useful in conjunction with fuels having any amount of sulfur including low-sulfur fuels of 0.5 wt % or less sulfur, is useful in ultra-low sulfur fuels having 0.1 wt % or less sulfur and no-sulfur fuels. For example, a fuel may have 0.5 wt % or less sulfur, or 0.1 wt % or less sulfur, or 0 wt % to 0.5 wt % sulfur, or 0.01 wt % to 0.5 wt % sulfur, or 0.01 wt % to 0.1 wt % sulfur, or 0 wt % to 0.1 wt % sulfur.

Accordingly, a method of the present disclosure may comprise: measuring a first metal concentration (e.g., calcium or other another metal described herein) in a lubricating oil (e.g., marine lubricating oil) prior to introduction into a cylinder in an engine (e.g., a two-stroke engine) using x-ray fluorescence, wherein the first metal concentration includes a concentration of soluble metal and a concentration of insoluble metal; collecting a scrape-down lubricating oil (e.g., a scrape-down marine lubricating oil) that corresponds to the lubricating oil after having been passed through the cylinder during fuel combustion of a fuel (e.g., comprising 0.5 wt % or less sulfur, comprising 0.1 wt % sulfur or less, or comprising no sulfur); measuring a second metal concentration in the scrape-down lubricating oil using the x-ray fluorescence; calculating a change in metal concentration between the lubricating oil and the scrape-down lubricating oil during combustion based on the first and second metal concentration; and when the change in metal concentration is an increase in the metal concentration that is above a threshold, implementing a change to a property of the scrape-down marine lubricating oil and/or changing a feed rate of the lubricating oil into the cylinder to cause a reduction in a base number of the lubricating oil in the engine.

Analyzing lubricating oil in the present disclosure may include determining one or more of: (a1) an amount of acid neutralized during combustion for a scrape-down lubricating oil, (b1) an amount of acid neutralized during combustion for a scrape-down lubricating oil and a remaining useful base number for the scrape-down lubricating oil, (c1) an amount of acid neutralized during combustion for a scrape-down lubricating oil and a total base number for the scrape-down lubricating oil, or (d1) a change in metal concentration between the lubricating oil and the scrape-down lubricating oil. Based on one or more of the foregoing, a change to a property of the scrape-down marine lubricating oil and/or changing a feed rate of the lubricating oil may be implemented to mitigate the formation of precipitates in the lubricating oil in the engine (e.g., by causing a reduction in the base number of the lubricating oil in the engine).

EXAMPLE EMBODIMENTS

Embodiment 1

A method comprising: measuring a first concentration of components in a lubricating oil prior to introduction into a cylinder in a two-stroke engine using x-ray fluorescence, the components comprising: sulfur and total calcium; collecting a scrape-down lubricating oil that corresponds to the lubricating oil after having been passed through the cylinder during fuel combustion of a fuel comprising 0.5 wt % or less sulfur; measuring a second concentration of the components in the scrape-down lubricating oil using the x-ray fluorescence; and calculating an amount of acid neutralized during combustion based on the first and second concentration of the components.

Embodiment 2

The method of Embodiment 1 further comprising: implementing a change to a property of the scrape-down lubricating oil and/or changing a feed rate of the lubricating oil into the cylinder based on the amount of acid neutralized.

Embodiment 3

The method of any one of Embodiments 1-2, wherein the measuring of the second concentration of the components is within about 4 hours of the collecting of the scrape-down lubricating oil.

Embodiment 4

The method of any one of Embodiments 1-3, wherein the implanting of the change to the property and/or the changing of the feed rate is further based on a remaining useful base number that equals a total base number of the lubricating oil prior to introduction into the cylinder (TBNfresh) minus the amount of acid neutralized.

Embodiment 5

The method of any one of Embodiments 1-4, wherein the fuel comprises 0.1 wt % or less of sulfur.

Embodiment 6

The method of any one of Embodiments 1-5 further comprising: measuring a concentration of one or more elements of: iron, chromium, or vanadium; and wherein the implanting of the change to the property and/or the changing of the feed rate is further based on the concentration of the one or more elements.

Embodiment 7

A method comprising: measuring a first concentration of components in a lubricating oil prior to introduction into a cylinder in an engine using x-ray fluorescence, the components comprising: sulfur and total calcium; collecting a scrape-down lubricating oil that corresponds to the lubricating oil after having been passed through the cylinder during fuel combustion of a fuel comprising 0.5 wt % or less sulfur; measuring a second concentration of the components in the scrape-down lubricating oil using the x-ray fluorescence; and calculating an amount of acid neutralized during combustion based on the first and second concentration of the components; calculating a remaining useful base number for the scrape-down lubricating oil.

Embodiment 8

A method comprising: measuring a first concentration of components in a lubricating oil prior to introduction into a cylinder in an engine using x-ray fluorescence, the components comprising: sulfur and total calcium; collecting a scrape-down lubricating oil that corresponds to the lubricating oil after having been passed through the cylinder during fuel combustion of a fuel comprising 0.5 wt % or less sulfur; measuring a second concentration of the components in the scrape-down lubricating oil using the x-ray fluorescence; and calculating an amount of acid neutralized during combustion based on the first and second concentration of the components; calculating a total base number for the scrape-down lubricating oil.

Embodiment 9

A method comprising: measuring a first concentration of components in a lubricating oil prior to introduction into a cylinder in an engine using x-ray fluorescence, the components comprising: sulfur and total calcium; collecting a scrape-down lubricating oil that corresponds to the lubricating oil after having been passed through the cylinder during fuel combustion of a fuel comprising 0.5 wt % or less sulfur; measuring a second concentration of the components in the scrape-down lubricating oil using the x-ray fluorescence; and calculating an amount of acid neutralized during combustion based on the first and second concentration of the components; calculating (a) a remaining useful base number for the scrape-down lubricating oil and/or (b) a total base number for the scrape-down lubricating oil.

Embodiment 10

The method of any one of Embodiments 7-9 further comprising: implementing a change to a property of the scrape-down lubricating oil and/or changing a feed rate of the lubricating oil into the cylinder (e.g., based on based on the remaining useful base number for Embodiment 8, based on a correlation between the amount of acid neutralized during combustion and the total base number for the scrape-down lubricating oil for Embodiment 9, or based on (a) the remaining useful base number and/or (b) a correlation between the amount of acid neutralized during combustion and the total base number for the scrape-down lubricating oil for Embodiment 10).

Embodiment 11

The method of any one of Embodiments 7-10, wherein the measuring of the second concentration of the components is within about 4 hours of the collecting of the scrape-down lubricating oil.

Embodiment 12

The method of any one of Embodiments 7-11, wherein the fuel comprises 0.1 wt % or less of sulfur.

Embodiment 13

The method of any one of Embodiments 7-12 further comprising: measuring a concentration of one or more elements of: iron, chromium, or vanadium; and wherein the implanting of the change to the property and/or the changing of the feed rate is further based on the concentration of the one or more elements.

Embodiment 14

A method comprising: measuring a first metal concentration in a marine lubricating oil prior to introduction into a cylinder in an engine using x-ray fluorescence, wherein the first metal concentration includes a concentration of soluble metal and a concentration of insoluble metal; collecting a scrape-down marine lubricating oil that corresponds to the marine lubricating oil after having been passed through the cylinder during fuel combustion of a fuel comprising 0.5 wt % or less sulfur; measuring a second metal concentration in the scrape-down marine lubricating oil using the x-ray fluorescence; calculating a change in metal concentration during combustion based on the first and second metal concentration; and when the change in metal concentration is an increase in the metal concentration that is above a threshold, implementing a change to a property of the scrape-down marine lubricating oil and/or changing a feed rate of the lubricating oil into the cylinder to cause a reduction in a base number of the lubricating oil in the engine.

Embodiment 15

The method of Embodiment 14, wherein the fuel contains 0.1 wt % sulfur or less.

Embodiment 16

The method of any one of Embodiments 14-15, wherein the fuel contains no sulfur.

Embodiment 17

The method of any one of Embodiments 14-16, wherein the metal is selected from the group consisting of: iron, chromium, vanadium, magnesium, phosphorus, chlorine, potassium, manganese, aluminum, silicon, titanium, copper, nickel, zinc, lead, tin, or other elements

Embodiment 18

The method of any one of Embodiments 14-17, wherein the metal is calcium.

Embodiment 19

The method of Embodiment 18 further comprising: wherein the fuel contains sulfur, measuring a first concentration of sulfur in the lubricating oil; measuring a second concentration of sulfur in the scrape-down lubricating oil; calculating an amount of acid neutralized during combustion based on the first and second concentration of the components; and wherein the implanting of the change to the property and/or the changing of the feed rate is further based on the amount of acid neutralized.

Embodiment 20

The method of Embodiment 19 further comprising: calculating a remaining useful base number for the scrape-down marine lubricating oil; and wherein the implanting of the change to the property and/or the changing of the feed rate is further based on the remaining useful base number.

Embodiment 21

The method of Embodiment 19 further comprising: calculating a total base number for the scrape-down lubricating oil; and wherein the implanting of the change to the property and/or the changing of the feed rate is further based on a correlation between the amount of acid neutralized during combustion and the total base number for the scrape-down lubricating oil.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the incarnations of the present inventions. At the very least, and not as an attempt to limit the application of the doctrine of equivalents to the scope of the claim, each numerical parameter should at least be construed in light of the number of reported significant digits and by applying ordinary rounding techniques.

One or more illustrative incarnations incorporating one or more invention elements are presented herein. Not all features of a physical implementation are described or shown in this application for the sake of clarity. It is understood that in the development of a physical embodiment incorporating one or more elements of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having the benefit of this disclosure.

While compositions and methods are described herein in terms of "comprising" various components or steps, the compositions and methods can also "consist essentially of" or "consist of" the various components and steps.

Additional Embodiments

To facilitate a better understanding of the embodiments of the present invention, the following examples of preferred or representative embodiments are given. In no way should the following examples be read to limit, or to define, the scope of the invention.

EXAMPLES

Example 1

A plurality of marine oil samples (both fresh and scrape-down) undergoing different treatments were analyzed by titration and by TBN (EQ. 6 using XRF, unless otherwise specified).

TABLE 1

| Sample Number | Sample Composition and Treatment | D2896 Titrated TBN | TBN via Algorithm | Ca (wt %) | Fe (ppm) | S (wt %) |
|---|---|---|---|---|---|---|
| 1 | Fresh MG5100 | 102 | 101 (EQ. 4) | 3.75 | 4 | 1.29 |
| | | | Scrape-down Samples | | | |
| 2 | MG5100 Scrape-down oil (collected, analyzed on-board) | n/a | 51 | 4.65 | 176 | 3.69 |
| 3 | MG5100 Scrape-down oil (sample 2 analyzed in lab 3 weeks later with shaking but no scraping before analysis) | 36.2 | 40 | 3.78 | 124 | 3.01 |
| 4 | MG5100 Scrape-down oil (sample 2 analyzed in lab 3 weeks later with shaking and scraping before analysis) | n/a | 48 | 4.19 | 176 | 3.27 |
| 5 | MG5100 Scrape-down oil (sample 2 analyzed in lab 3 weeks later with shaking but no scraping and then settling 4 hours before analysis) | n/a | 42 | 3.84 | 167 | 3.07 |
| | | | Controlled Laboratory Experiments | | | |
| 6 | Fresh MG5100 treated with 2 wt % CaCO$_3$ (prepared, analyzed) | 100 | 116 | 4.18 | 10 | 1 |

TABLE 1-continued

| Sample Number | Sample Composition and Treatment | D2896 Titrated TBN | TBN via Algorithm | Ca (wt %) | Fe (ppm) | S (wt %) |
|---|---|---|---|---|---|---|
| 7 | Fresh MG5100 treated with 2 wt % CaCO₃ (prepared, settled 4 hours, analyzed) | n/a | 104 | 3.89 | 8 | 1.02 |
| 8 | Fresh MG5100 treated with 2 wt % CaCO₃ (prepared, settled over weekend, analyzed) | n/a | 100 | 3.79 | 7.9 | 1.01 |

This series of analyses illustrates that delay between the collection of the sample and analysis for determination of TBN causes the TBN values to become more inaccurate, which is likely due to calcium carbonate settling and not being accounted for in the measurements.

Example 2

A plot of TBN use d (EQ. 3) as a function of acid neutralized (A.N.) is illustrated in FIG. 1 using data from various marine lubricant samples. Using the correlations provided in FIG. 1, high $TBN_{used}$ (e.g., greater than about 100 mg KOH/g lubricant) corresponding to a low A.N. (e.g., less than about 30 mg KOH/g lubricant) may indicate that significant amounts of calcium carbonate are forming solid particulates and causing wear to the engine. Further, a low TBN use d (e.g., less than about 50 mg KOH/g lubricant) and a low A.N. (e.g., less than about 30 mg KOH/g lubricant) may indicate that appropriate conditions and compositions are in place and should be maintained.

Example 3

Figure 2:
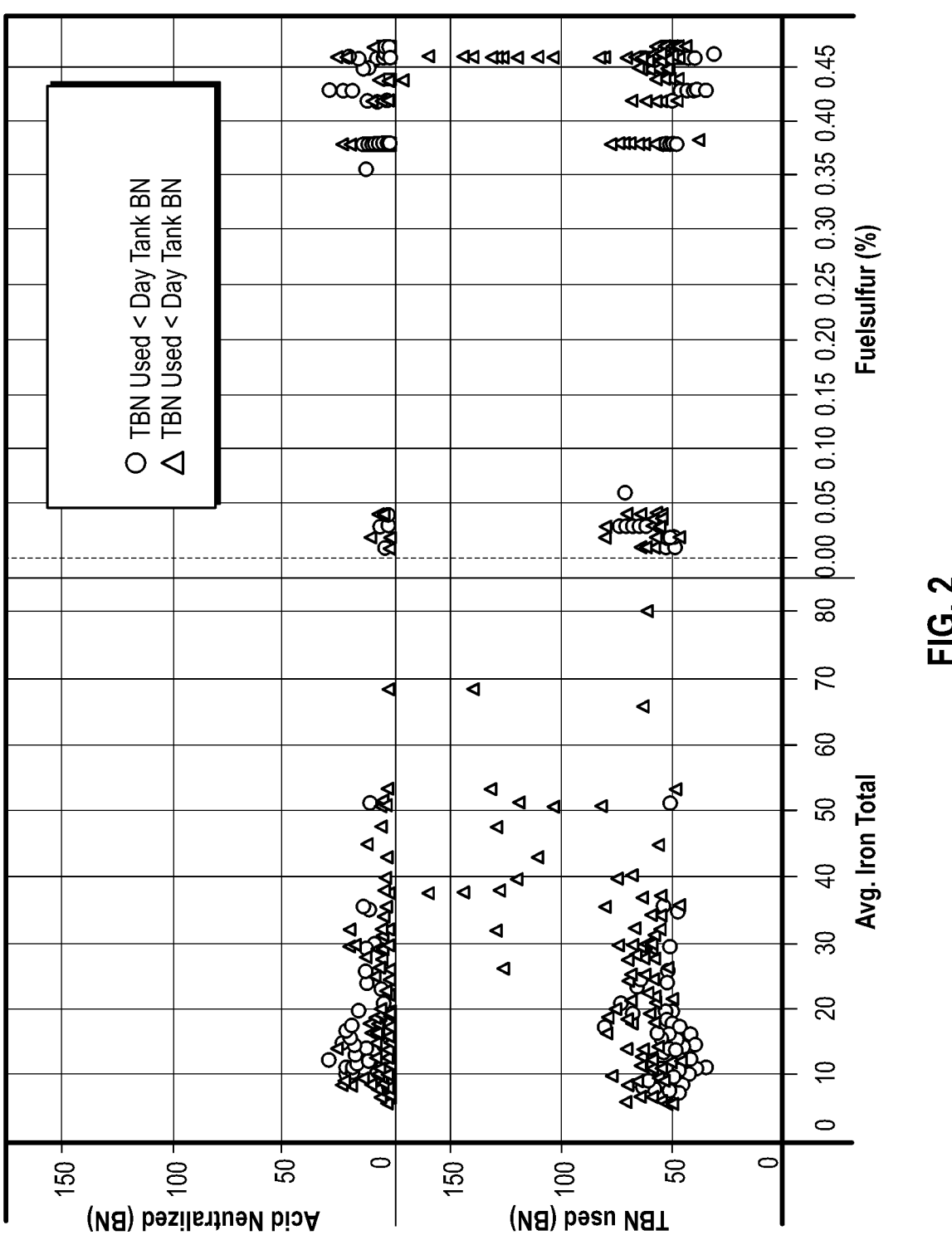
FIG. 2 illustrates four plots of total base number used ($TBN_{used}$) (EQ. 3) or acid neutralized (A.N.) each as a function of average total iron (as determined by x-ray fluorescence) or fuel sulfur percent from various marine lubricant samples.

Plots of TBN use d (EQ. 3) or acid neutralized (A.N.) each as a function of average total iron (as determined by XRF) or fuel sulfur percent are illustrated in FIG. 2 using data from various marine lubricant samples. Using the correlations provided in FIG. 2, high TBN use d (e.g., greater than about 100 mg KOH/g lubricant) corresponding to a high iron may indicate wear to the engine and high TBN use d corresponding to high fuel sulfur percent may indicate that significant amounts of calcium carbonate are forming solid particulates and causing wear to the engine. In contrast, similar plots with A.N. rather than TBN used do not elucidate these features, thereby illustrating the advantages of using TBN use d correlations of the present disclosure.

Example 4

Figure 3:
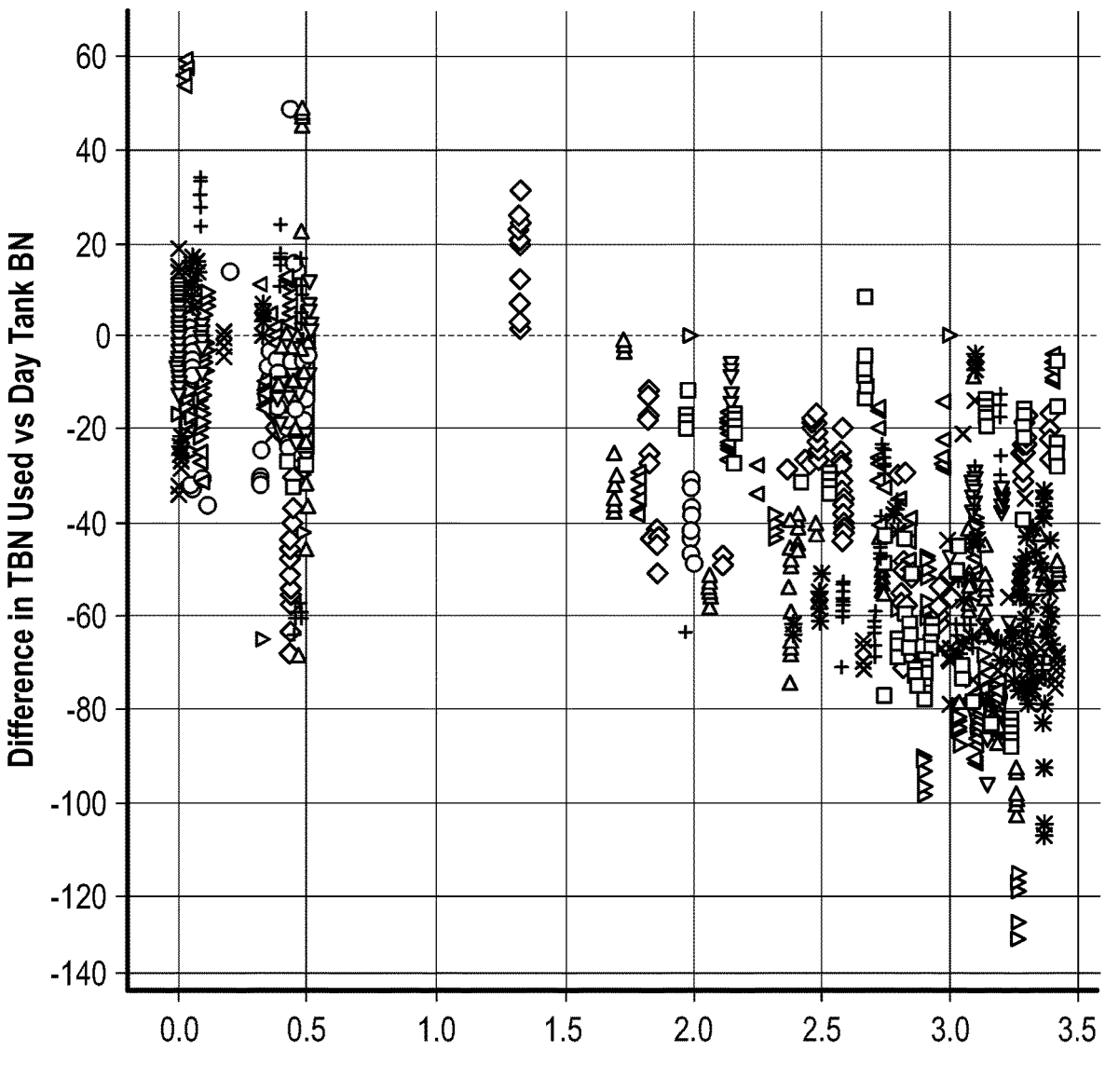
FIG. 3 is a plot of the difference between TBN used and Day Tank BN for various marine lubricant samples as a function of fuel sulfur percent.

FIG. 3 is a plot (of the differences between TBN use d and Day Tank BN for various marine lubricant samples as a function of fuel sulfur percent. At low fuel sulfur percent, some differences are positive indicating that the Day Tank BN is higher than the TBN use d.

Example 5

Figure 4:
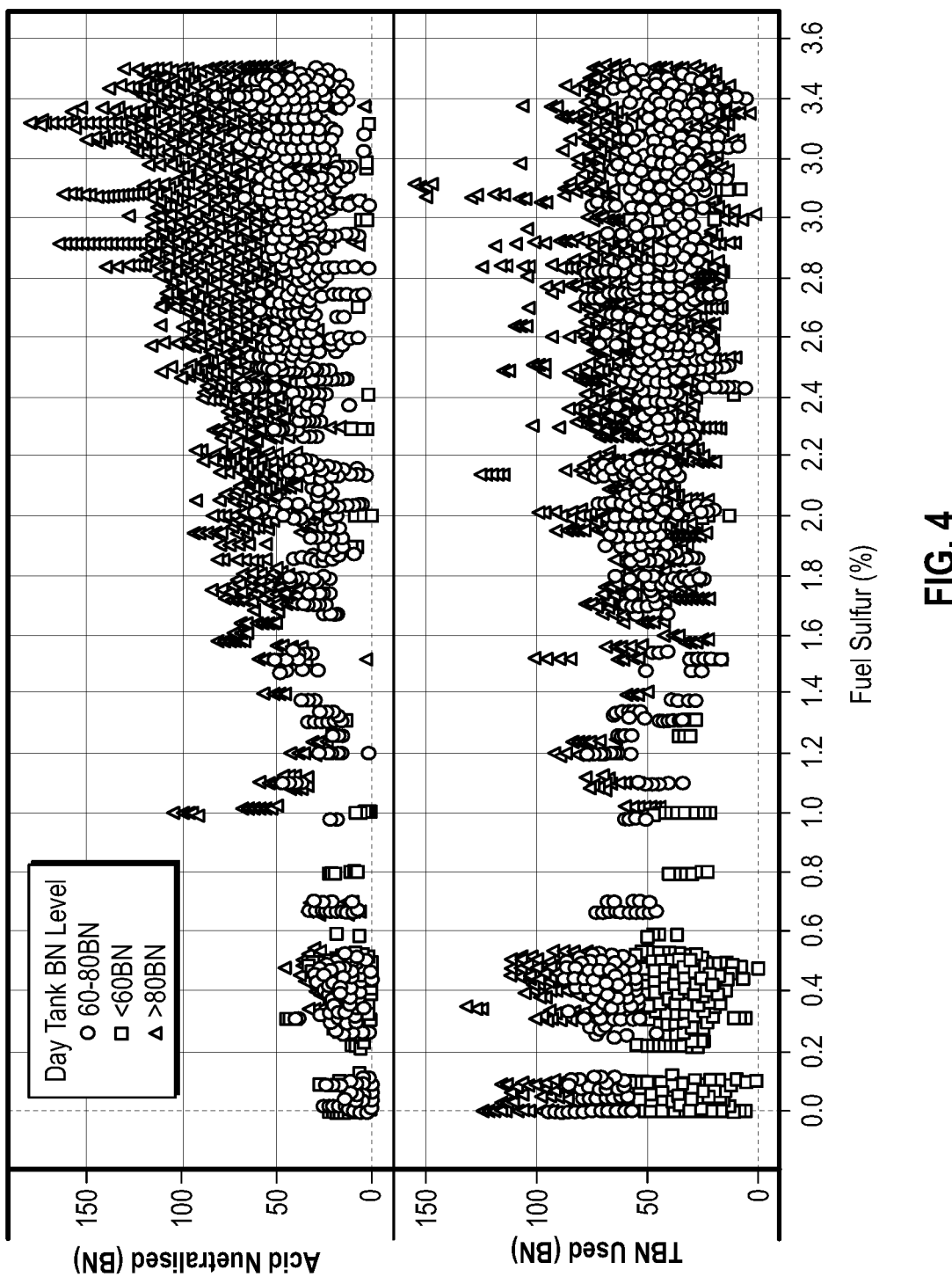
FIG. 4 is a plot of $TBN_{used}$ or A.N. for various marine lubricant samples as a function of fuel sulfur percent.
Figure 5A:
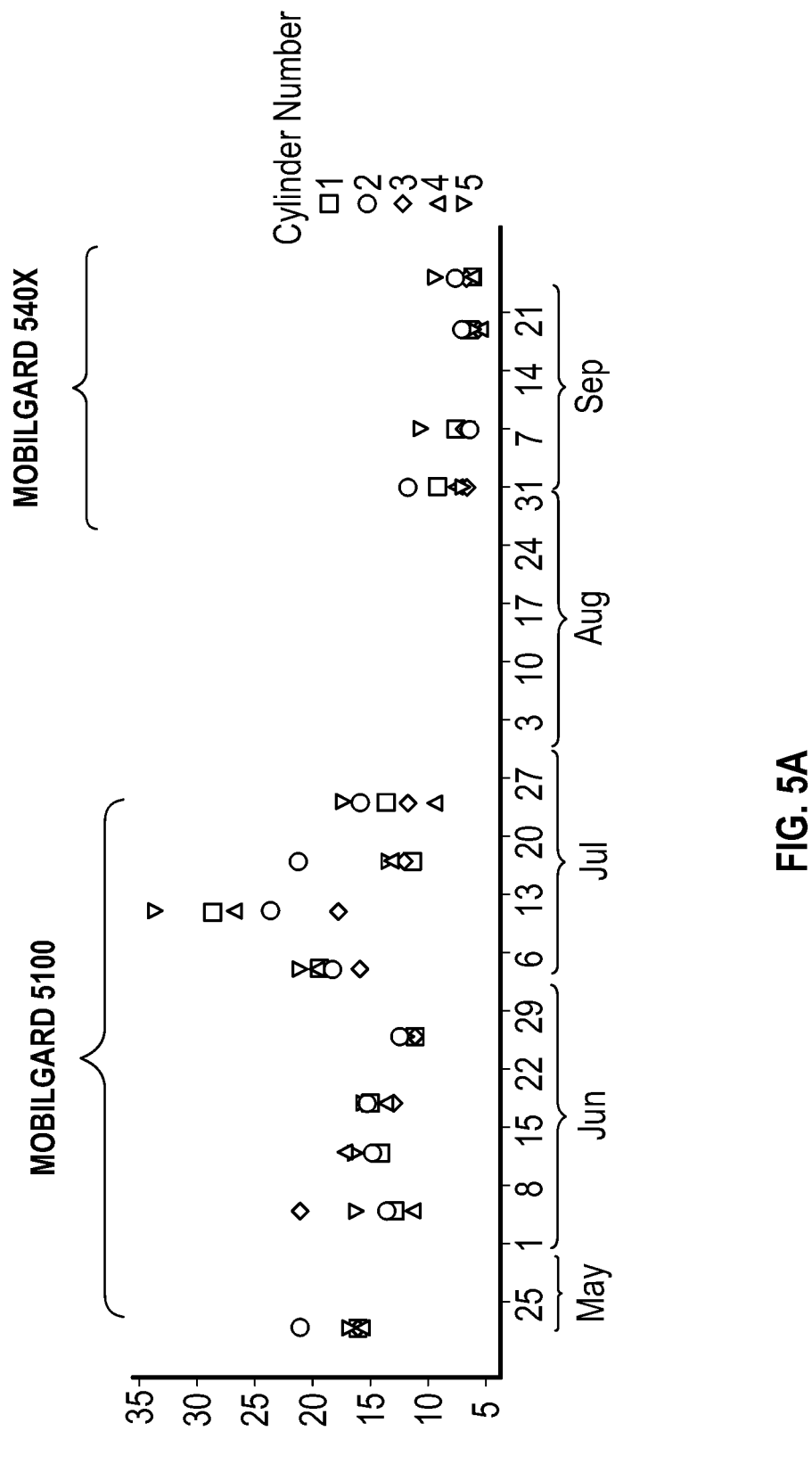
FIGS. 5A-B are plots of the iron concentrations (A) and calcium concentrations (B) as a function of time for Engine 1.
Figure 5B:
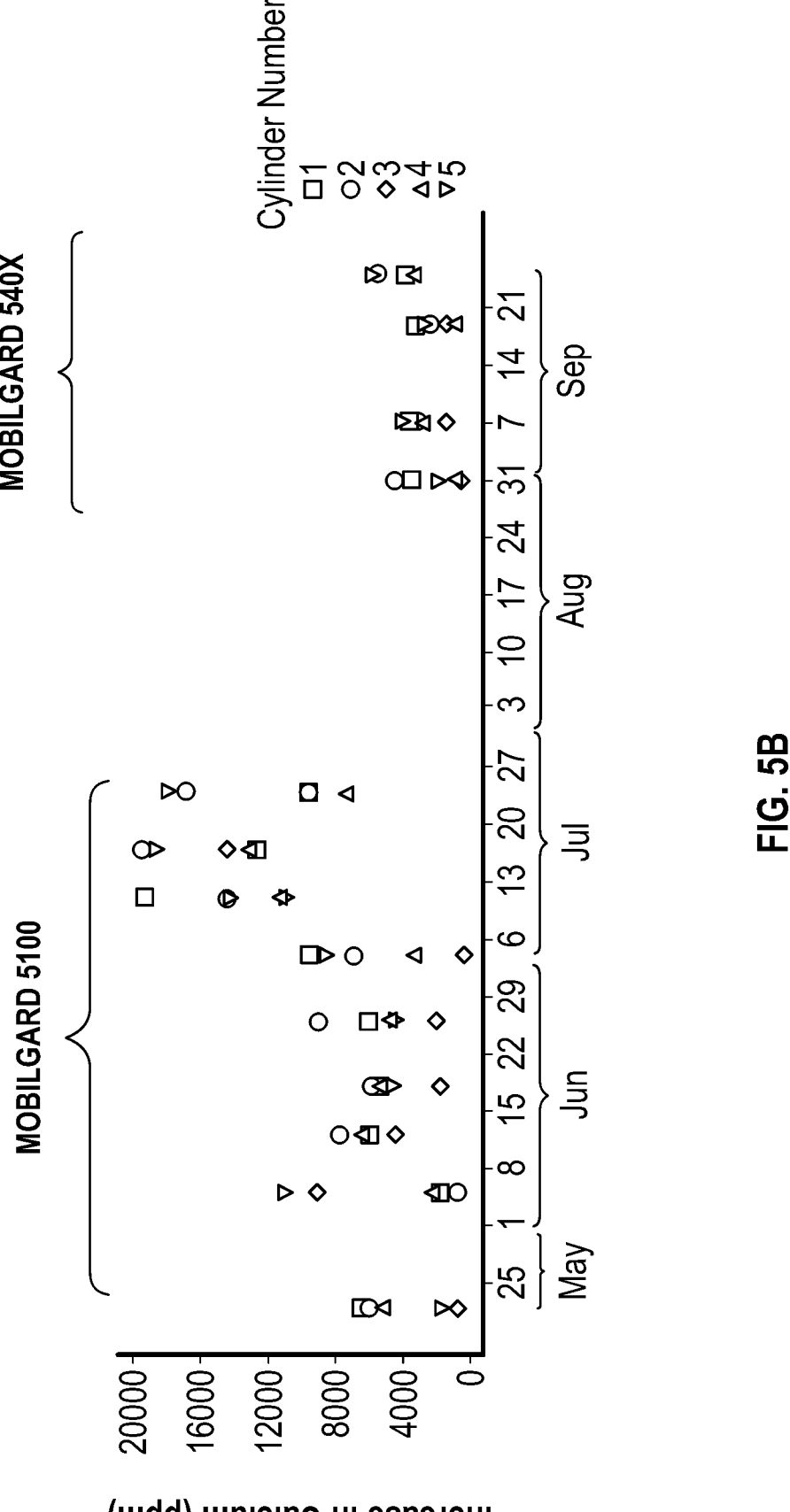
Figure 6A:
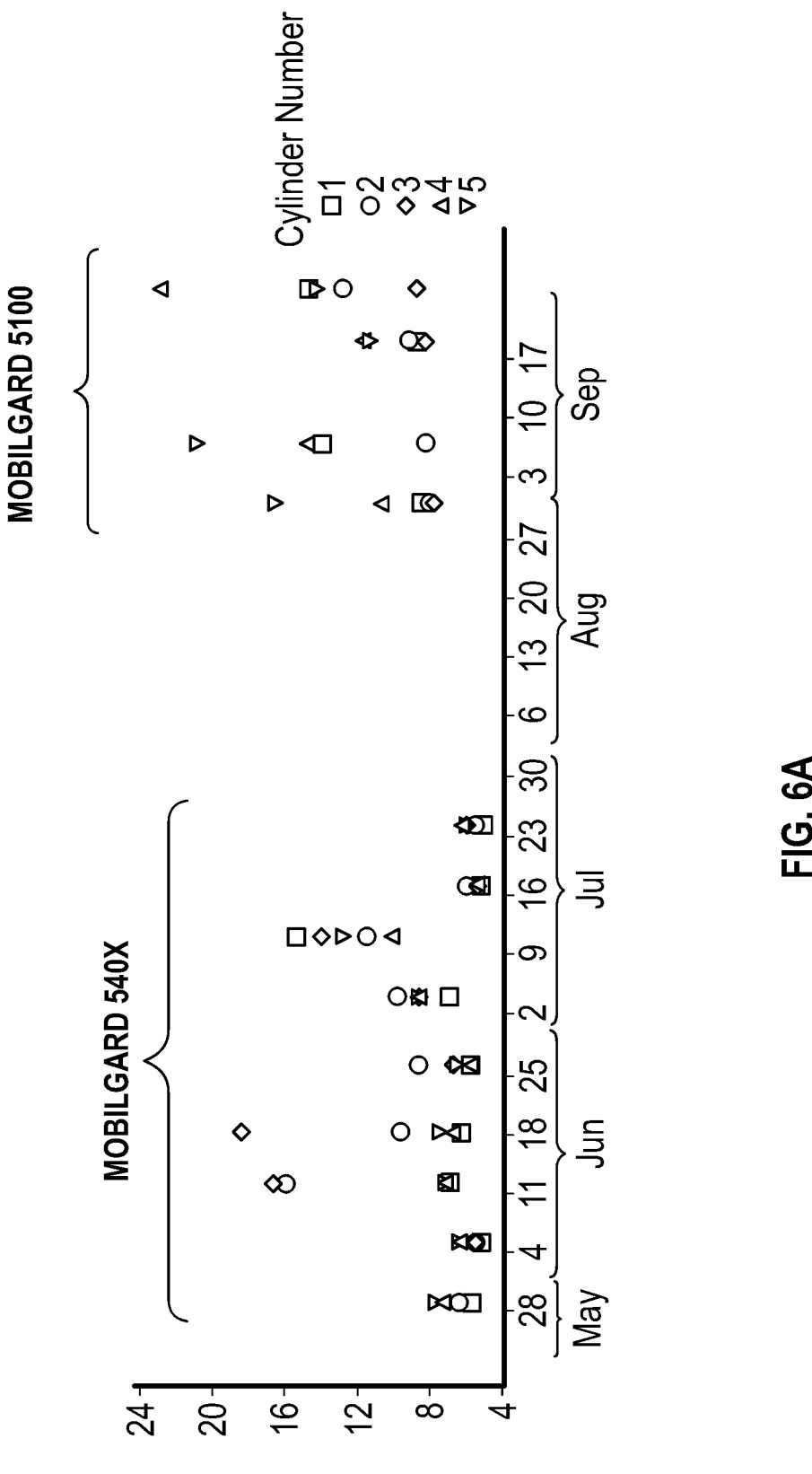
FIGS. 6A-B are plots of the iron concentrations (A) and calcium concentrations (B) as a function of time for Engine 2.
Figure 6B:
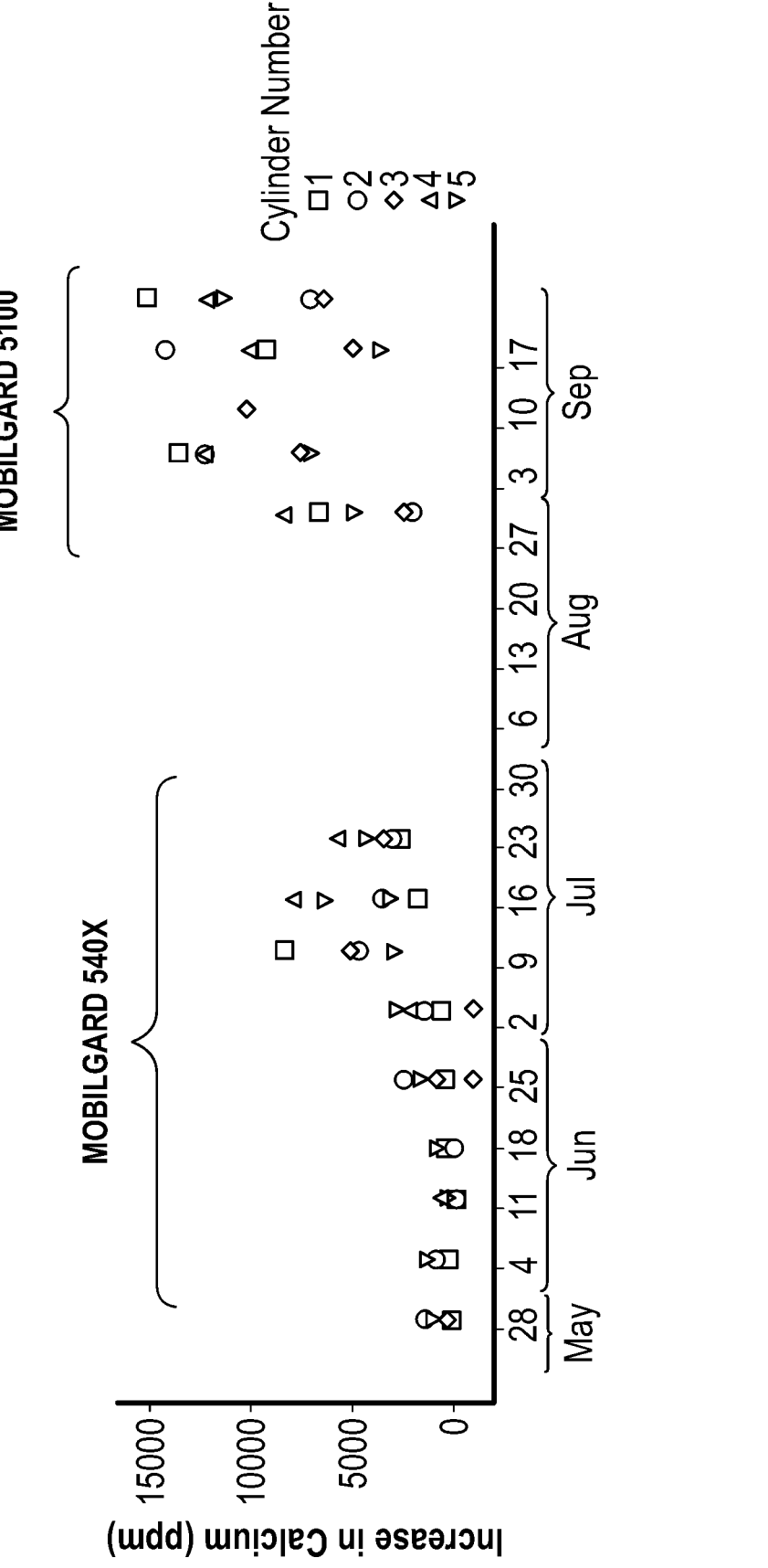

FIG. 4 illustrates a plot of TBN use d or A.N. for various marine lubricant samples as a function of fuel sulfur percent. At low fuel sulfur percent, all samples have similar A.N. values. However, when using TBN use d, additional information can be extracted from the data.

Example 6

A vessel with two identical engines were run with a 100 BN and a 40 BN lubricant on 0.09% sulfur fuel. Engine 1 was started with a 100 BN lubricant oil then switched to a 40 BN lubricant oil. Engine 2 was started with a 40 BN lubricant oil and switched to a 100 BN lubricant oil. Table 2 provides the data collected for each of the engines and lubricants. FIGS. 5A-B and 6A-B are plots of the iron concentrations (A) and calcium concentrations (B) as a function of time for Engines 1 and 2, respectively.

TABLE 2

| Description | Cylinder | ASTM D2896 Measured BN | OnBoard XRF BN (mg KOH/g) | Acid Neutralized (mg KOH/g) | Ca wt % OnBoard | Excess Ca wt % (Representation of potential CaCO₃ Deposits) | OnBoard Fe ppm |
|---|---|---|---|---|---|---|---|
| Engine 1 (MOBILGARD 5100, 100 BN cylinder oil, available from ExxonMobil) | | | | | | | |
| Day Tank Sample | Fresh | 102 | 102 | | 3.82 | | |
| Engine | 1 | 69 | 85 | 6 | 4.48 | 0.66 | 16 |
| Load 50%; | 2 | 73 | 83 | 6 | 4.30 | 0.48 | 21 |
| Fuel Sulfur | 3 | 66 | 72 | 7 | 4.02 | 0.20 | 16 |
| 0.09% | 4 | 79 | 91 | 5 | 4.34 | 0.52 | 16 |
| | 5 | 78 | 77 | 7 | 3.99 | 0.17 | 17 |
| Average | | | | | | 0.41 | 17.20 |

TABLE 2-continued

| Description | Cylinder | ASTM D2896 Measured BN | OnBoard XRF BN (mg KOH/g) | Acid Neutralized (mg KOH/g) | Ca wt % OnBoard | Excess Ca wt % (Representation of potential CaCO₃ Deposits) | OnBoard Fe ppm |
|---|---|---|---|---|---|---|---|
| Engine 2 (MOBILGARD 540X, 40 BN cylinder oil, available from ExxonMobil) | | | | | | | |
| Day Tank Sample | Fresh | | 43 | | 1.62 | | |
| Engine | 1 | 19 | 18 | 8 | 1.77 | 0.15 | 8 |
| Load 50%; | 2 | 22 | 18 | 8 | 1.78 | 0.16 | 7 |
| Fuel Sulfur | 3 | 21 | 18 | 9 | 1.69 | 0.07 | 8 |
| 0.09% | 4 | 23 | 27 | 7 | 1.84 | 0.22 | 9 |
| | 5 | 26 | 29 | 9 | 1.94 | 0.32 | 8 |
| Average | | | | | | 0.19 | 8.00 |
| Engine 1 (MOBILGARD 540X) | | | | | | | |
| Day Tank Sample | Fresh | | 45 | | 1.67 | | |
| Engine | 1 | | 40 | 2 | 2.00 | 0.33 | 9 |
| Load 57%; | 2 | | 44 | 1 | 2.02 | 0.35 | 12 |
| Fuel Sulfur | 3 | | 32 | 5 | 1.78 | 0.11 | 7 |
| 0.09% | 4 | | 32 | 4 | 1.66 | −0.01 | 8 |
| | 5 | | 33 | 4 | 1.69 | 0.02 | 7 |
| Average | | | | | | 0.16 | 8.60 |
| Engine 2 (MOBILGARD 5100) | | | | | | | |
| Day Tank Sample | Fresh | | 101 | | 3.78 | | |
| Engine | 1 | | 51 | 11 | 4.38 | 0.60 | 8.45 |
| Load 57%; | 2 | | 34 | 15 | 3.89 | 0.11 | 8 |
| Fuel Sulfur | 3 | | 34 | 13 | 3.64 | −0.14 | 5.6 |
| 0.09% | 4 | | 69 | 8 | 4.46 | 0.68 | 11 |
| | 5 | | 62 | 10 | 3.99 | 0.21 | 17 |
| Average | | | | | | 0.29 | 10.01 |

The 100 BN lubricant oil shows excess calcium in both engines, and with the higher excess calcium, higher iron wear values are also seen. The 40 BN oil, with high detergency to help solubilize excess calcium, shows less excess calcium and lower iron wear values. Low acid number with high residual BN in the 100 BN lubricant oil may be indicative of potential high wear due to excess deposit formation. Acid neutralized remains relatively constant with both cylinder oils indicating that 40 lubricant BN oil is more appropriate for this level of fuel sulfur and acid production. Lower lab D2896 measured base number may be indicative of what is missed with the lab analysis versus being able to analyze the sample fresh onboard the vessel and shows that lab analysis does not reveal wear causing deposits. Engine 2 had a system oil contamination issue which lead to lower than expected residual base number.

Example 7

Two vessels with similar engines with the same bore size were run with a 40 BN lubricant on 0.02% or 0.03% sulfur fuel. Vessel 2 employs an exhausts gas recirculation (EGR) system. Table 3 provides the data collected for each of the engines and lubricants.

TABLE 3

| Description | Cylinder | OnBoard XRF BN (mg KOH/g) | Acid Neutralized (mg KOH/g) | % Ca concentration change OnBoard (EQ. 8) | Excess Ca wt % (Representation of potential CaCO₃ Deposits) | OnBoard Fe ppm |
|---|---|---|---|---|---|---|
| Vessel 1 (MOBILGARD 540X, without EGR) | | | | | | |
| Engine Load | 1 | 40 | 10 | 20 | 0.32 | 21 |
| 85%; Fuel | 2 | 34 | 7 | 0 | 0 | 14 |
| Sulfur 0.02% | 3 | 35 | 11 | 10 | 0.15 | 19 |
| | 4 | 36 | 9 | 9 | 0.13 | 15 |
| | 5 | 44 | 7 | 22 | 0.35 | 22 |
| | 6 | 43 | 5 | 14 | 0.22 | 12 |
| Average | | 39 | 8 | 12.5 | 0.20 | 17 |
| Vessel 2 (MOBILGARD 540X, with EGR) | | | | | | |
| Engine Load | 1 | 68 | −6 | 22 | 0.42 | 40 |
| 74%; Fuel | 2 | 69 | −5 | 27 | 0.50 | 22 |
| Sulfur 0.03% | 3 | 76 | −7 | 37 | 0.69 | 20 |
| | 4 | 69 | −5 | 26 | 0.50 | 25 |
| | 5 | 74 | −6 | 35 | 0.67 | 40 |

TABLE 3-continued

| Description | Cylinder | OnBoard XRF BN (mg KOH/g) | Acid Neutralized (mg KOH/g) | % Ca concentration change OnBoard (EQ. 8) | Excess Ca wt % (Representation of potential CaCO₃ Deposits) | OnBoard Fe ppm |
|---|---|---|---|---|---|---|
|  | 6 | 80 | −8 | 42 | 0.80 | 18 |
| Average |  | 73 | −6 | 31.5 | 0.60 | 28 |

Based on the calcium concentration change, Vessel 2 is showing signs of accumulation of wear causing calcium deposits.

Figure 7:
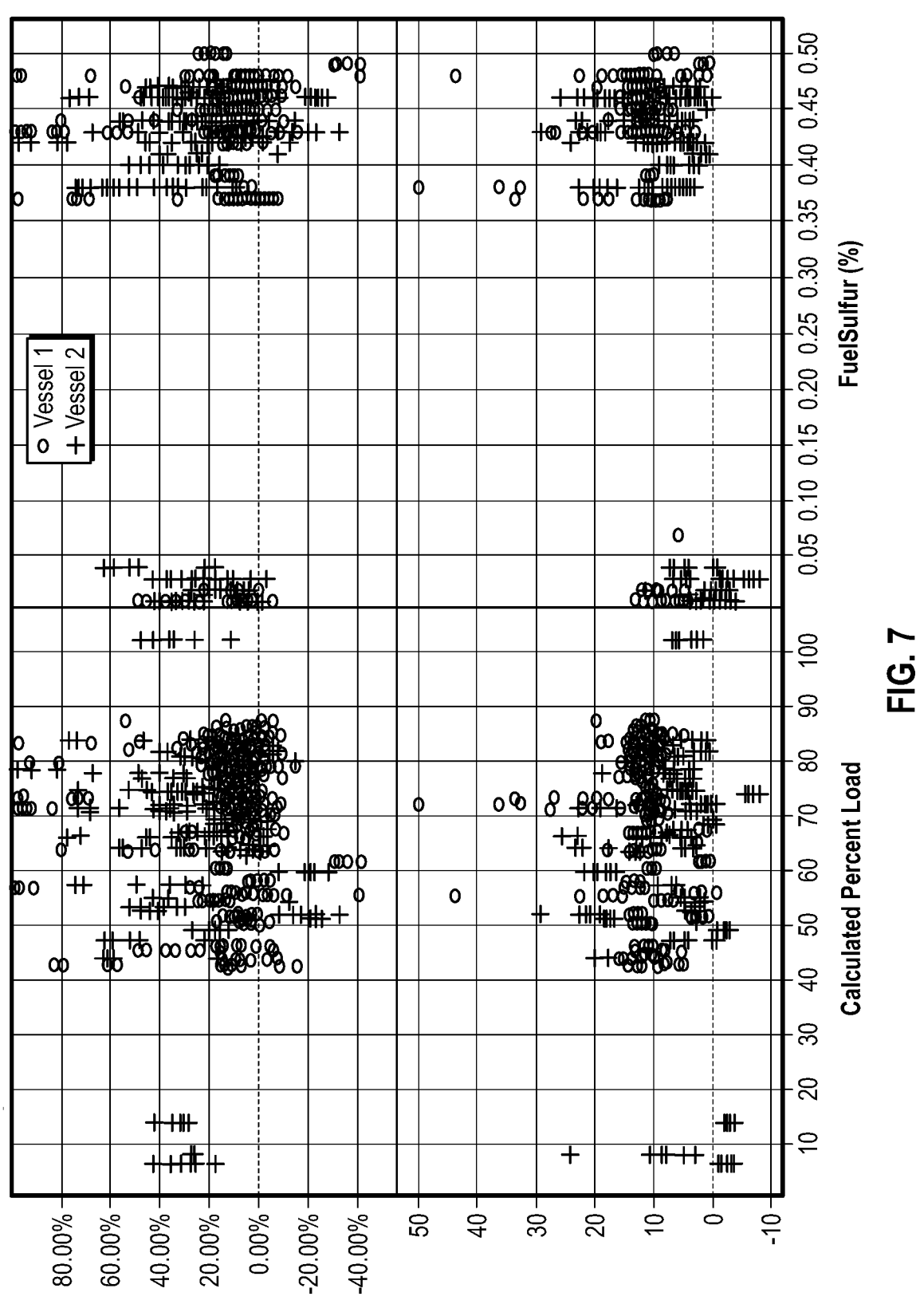
FIG. 7 includes four plots for either amount of acid neutralized or calcium concentration change as a function of percent load or fuel sulfur.

FIG. 7 includes four plots for either amount of acid neutralized or calcium concentration change (per EQ. 8) as a function of percent load or fuel sulfur. At higher fuel sulfur values, both the amount of acid neutralized and the calcium concentration change provide insight into the formation of calcium precipitates in the lubricating oil. However, at the lower sulfur fuel (below 0.1 wt %), the amount of acid neutralized appears to be steady and within a reasonable range. In contrast, the calcium concentration change for Vessel 2 has several data points above 20%, which indicates the formation of calcium deposits. This example illustrates that at fuel sulfur levels less than 0.1%, where there is very little sulfuric acid produced, calcium concentration provides a better indicator than acid neutralization for the formation of calcium deposits.

Upon visual inspection of portions of the engine, Vessel 1 showed light deposits of calcium. In contrast, Vessel 2 showed evidence of heavy deposit accumulation in the engine.

Therefore, the present invention is well adapted to attain the ends and advantages mentioned, as well as those that are inherent therein. The particular examples and configurations disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
measuring a first concentration of components in a lubricating oil prior to introduction into a cylinder in a two-stroke engine using x-ray fluorescence, the components comprising: sulfur and total calcium;
collecting a scrape-down lubricating oil that corresponds to the lubricating oil after having been passed through the cylinder during fuel combustion of a fuel comprising 0.5 wt % or less sulfur;
measuring a second concentration of the components in the scrape-down lubricating oil using the x-ray fluorescence; and
calculating an amount of acid neutralized during combustion based on the first and second concentration of the components.

2. The method of claim 1 further comprising:
implementing a change to a property of the scrape-down lubricating oil and/or changing a feed rate of the lubricating oil into the cylinder based on the amount of acid neutralized.

3. The method of claim 1, wherein the measuring of the second concentration of the components is within about 4 hours of the collecting of the scrape-down lubricating oil.

4. The method of claim 1, wherein the implanting of the change to the property and/or the changing of the feed rate is further based on a remaining useful base number that equals a total base number of the lubricating oil prior to introduction into the cylinder (TBN$_{fresh}$) minus the amount of acid neutralized.

5. The method of claim 1, wherein the fuel comprises 0.1 wt % or less of sulfur.

6. The method of claim 1 further comprising:
measuring a concentration of one or more elements of: iron, chromium, or vanadium; and
wherein the implanting of the change to the property and/or the changing of the feed rate is further based on the concentration of the one or more elements.

7. A method comprising:
measuring a first concentration of components in a lubricating oil prior to introduction into a cylinder in an engine using x-ray fluorescence, the components comprising: sulfur and total calcium;
collecting a scrape-down lubricating oil that corresponds to the lubricating oil after having been passed through the cylinder during fuel combustion of a fuel comprising 0.5 wt % or less sulfur;
measuring a second concentration of the components in the scrape-down lubricating oil using the x-ray fluorescence;
calculating an amount of acid neutralized during combustion based on the first and second concentration of the components; and
calculating (a) a remaining useful base number for the scrape-down lubricating oil and/or (b) a total base number for the scrape-down lubricating oil.

8. The method of claim 7 further comprising:

implementing a change to a property of the scrape-down lubricating oil and/or changing a feed rate of the lubricating oil into the cylinder based on (a) the remaining useful base number and/or (b) a correlation between the amount of acid neutralized during combustion and the total base number for the scrape-down lubricating oil.

9. The method of claim 7, wherein the measuring of the second concentration of the components is within about 4 hours of the collecting of the scrape-down lubricating oil.

10. The method of claim 7, wherein the fuel comprises 0.1 wt % or less of sulfur.

11. The method of claim 7 further comprising:

measuring a concentration of one or more elements of: iron, chromium, or vanadium; and wherein the implanting of the change to the property and/or the changing of the feed rate is further based on the concentration of the one or more elements.

12. A method comprising:

measuring a first metal concentration in a marine lubricating oil prior to introduction into a cylinder in an engine using x-ray fluorescence, wherein the first metal concentration includes a concentration of soluble metal and a concentration of insoluble metal;

collecting a scrape-down marine lubricating oil that corresponds to the marine lubricating oil after having been passed through the cylinder during fuel combustion of a fuel comprising 0.5 wt % or less sulfur;

measuring a second metal concentration in the scrape-down marine lubricating oil using the x-ray fluorescence;

calculating a change in metal concentration during combustion based on the first and second metal concentration; and when the change in metal concentration is an increase in the metal concentration that is above a threshold, implementing a change to a property of the scrape-down marine lubricating oil and/or changing a feed rate of the lubricating oil into the cylinder to cause a reduction in a base number of the lubricating oil in the engine.

13. The method of claim 12, wherein the fuel contains 0.1 wt % sulfur or less.

14. The method of claim 12, wherein the fuel contains no sulfur.

15. The method of claim 12, wherein the metal is selected from the group consisting of: iron, chromium, vanadium, magnesium, phosphorus, chlorine, potassium, manganese, aluminum, silicon, titanium, copper, nickel, zinc, lead, tin, or other elements.

16. The method of claim 12, wherein the metal is calcium.

17. The method of claim 16 further comprising:

measuring a first concentration of sulfur in the lubricating oil;

measuring a second concentration of sulfur in the scrape-down lubricating oil; and calculating an amount of acid neutralized during combustion based on the first and second concentration of the components; and wherein the implanting of the change to the property and/or the changing of the feed rate is further based on the amount of acid neutralized.

18. The method of claim 17 further comprising:

calculating a remaining useful base number for the scrape-down marine lubricating oil; and wherein the implanting of the change to the property and/or the changing of the feed rate is further based on the remaining useful base number.

19. The method of claim 17 further comprising:

calculating a total base number for the scrape-down lubricating oil; and wherein the implanting of the change to the property and/or the changing of the feed rate is further based on a correlation between the amount of acid neutralized during combustion and the total base number for the scrape-down lubricating oil.

* * * * *